United States Patent [19]

Collins

[11] Patent Number: 5,370,601
[45] Date of Patent: Dec. 6, 1994

[54] EXTERNAL PENILE ERECTION PROSTHESIS

[76] Inventor: Moseley C. Collins, 110 Elwa Pl., West Palm Beach, Fla. 33405

[21] Appl. No.: 200,206

[22] Filed: Feb. 23, 1994

Related U.S. Application Data

[63] Continuation-in-part of Ser. No. 978,490, Nov. 18, 1992, Pat. No. 5,295,946.

[51] Int. Cl.⁵ .............................................. A61F 5/41
[52] U.S. Cl. ...................................................... 600/41
[58] Field of Search .............................. 600/38, 39, 41

[56] References Cited

U.S. PATENT DOCUMENTS

| | | | |
|---|---|---|---|
| 4,407,275 | 11/1981 | Schroeder | 128/79 |
| 4,641,638 | 2/1987 | Perry | 128/79 |
| 4,834,115 | 5/1989 | Stewart | 600/41 |

FOREIGN PATENT DOCUMENTS

| | | | |
|---|---|---|---|
| 476413 | 2/1928 | Germany | 600/41 |
| 565238 | 11/1932 | Germany | 600/41 |

Primary Examiner—Cary E. O'Connor
Attorney, Agent, or Firm—Alvin S. Blum

[57] ABSTRACT

A device for affecting or enhancing erection of the penis comprises an external inflatable cuff which encircles the shaft of the penis at its base and extends distally. The cuff is provided with a plurality of volume expandable annular spaces arranged parallel to one another. The spaces are filled with fluid under pressure from a squeeze bulb to affect a tourniquet action. The spaces are inflated sequentially in a proximal to distal direction. As the spaces become sequentially pressurized, the inner diameter of the cuff is reduced, constricting the penis and trapping blood within the shaft and forcing it distally to thereby increase the rigidity of the penis.

12 Claims, 2 Drawing Sheets

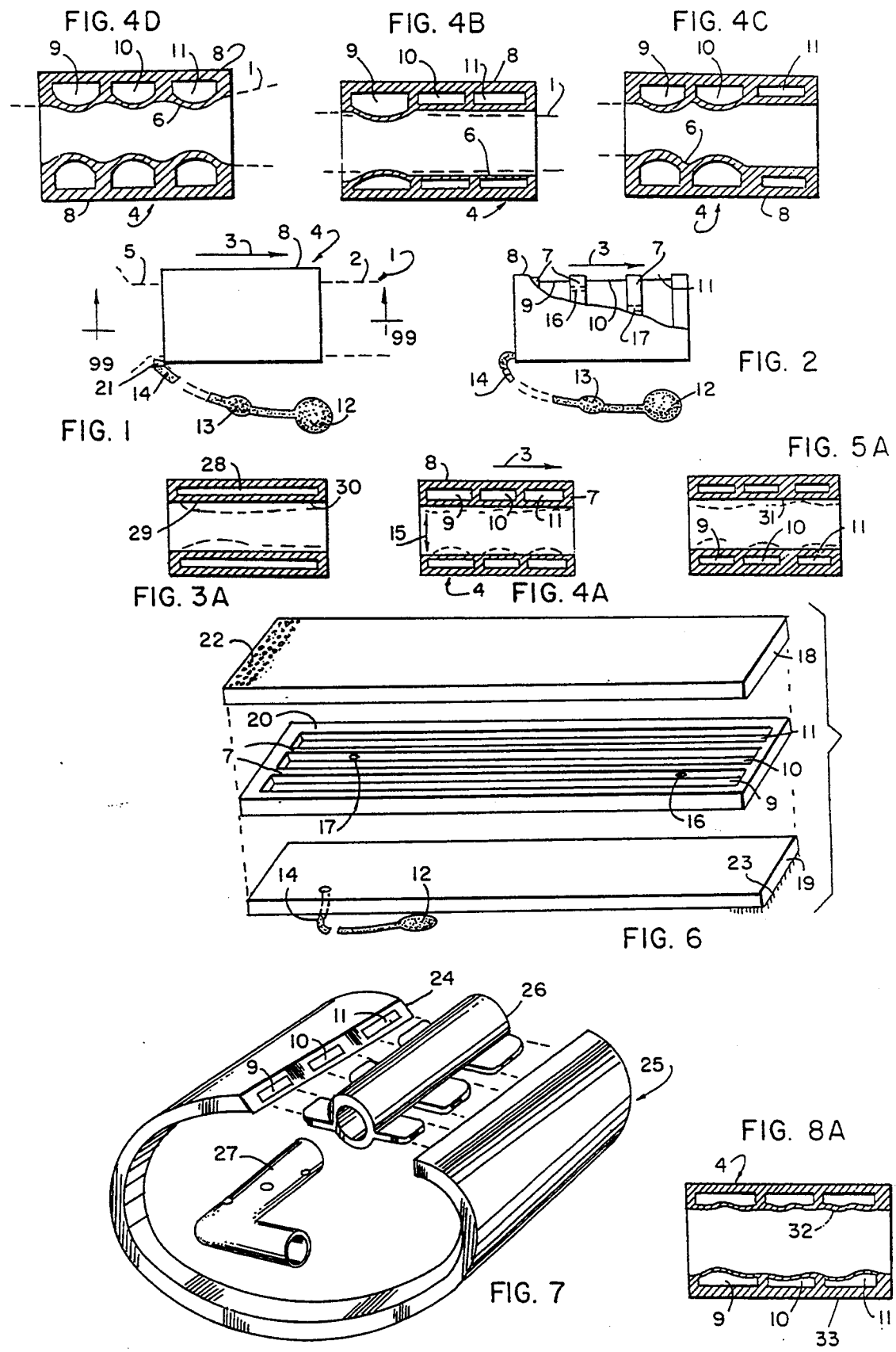

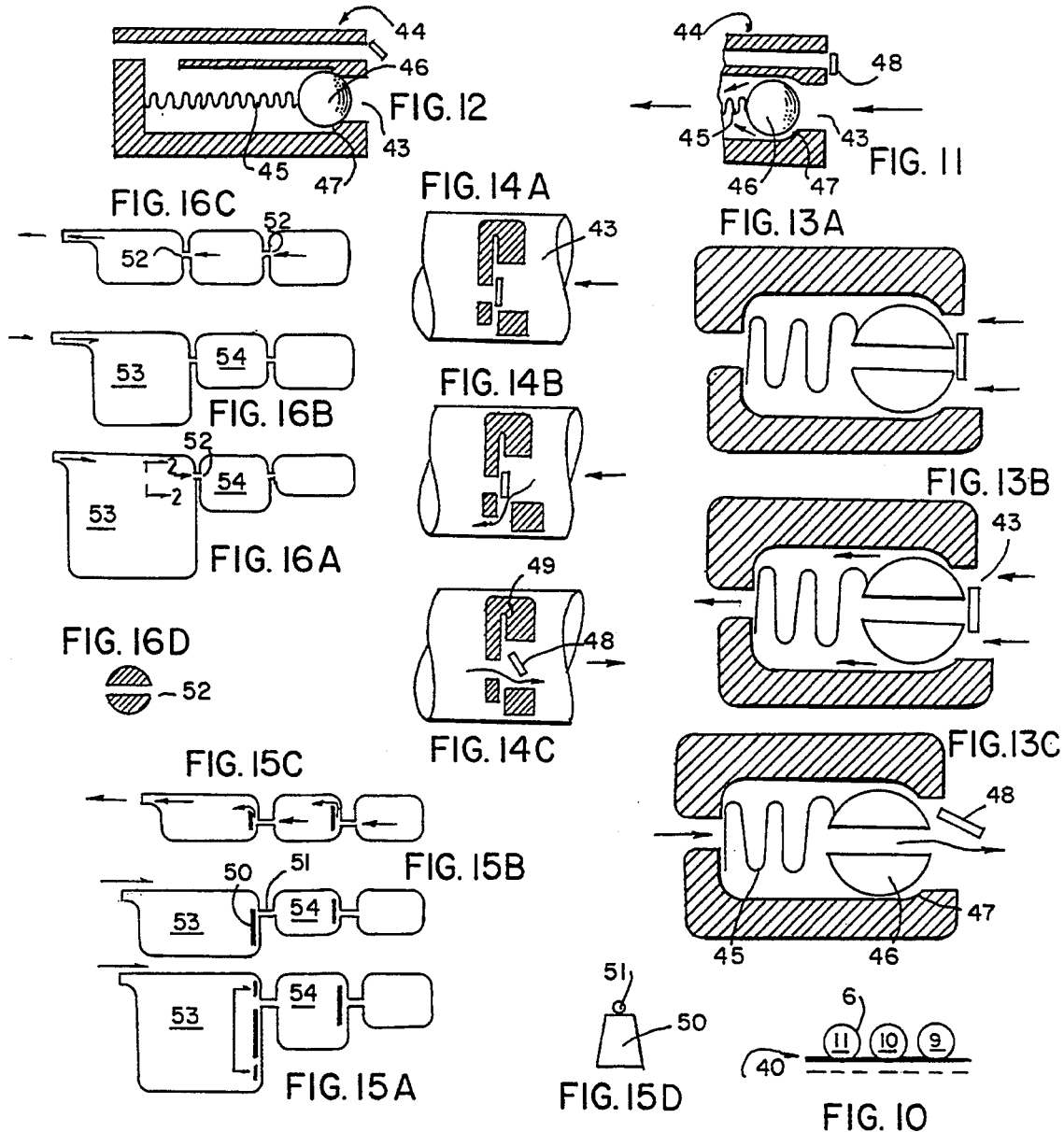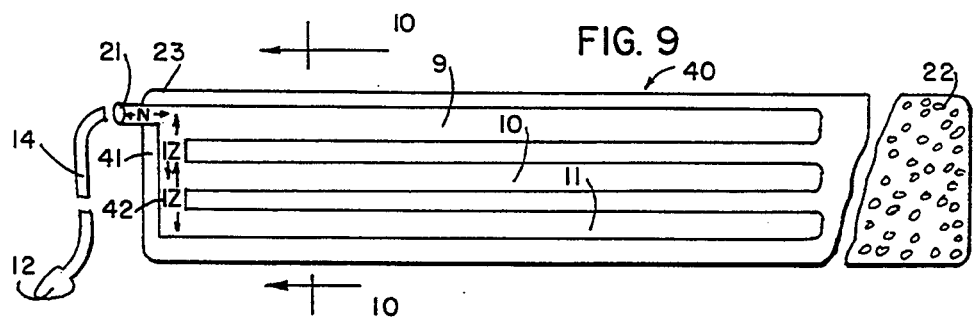

EXTERNAL PENILE ERECTION PROSTHESIS

This is a continuation in part of applicant's copending application Ser. No. 07/978,490 filed Nov. 18, 1992, now U.S. 5,295,946.

BACKGROUND OF THE INVENTION

This invention relates to devices for overcoming male impotence and more particularly to a device applied externally to the shaft of the penis that inflates to constrict the shaft to enhance rigidity.

With advancing age, and also in certain pathological conditions, men may not be able to achieve an erection with sufficient rigidity for satisfactory coitis. Various devices of the prior art for overcoming the problem are surgically implanted within the penis. Some are permanently rigid and hinged. Others provide a flaccid inflatable chamber which becomes rigid when inflated with fluid. The inflating apparatus is also implanted within the body. These invasive procedures destroy normal tissue, they are attended by the usual surgical risks, such as infection and hemorrhage, and they are not always successful. There is little chance of restoring normal function when they are removed.

There is no way to temporarily try the devices to predict success following the operation. It is devastating to go through the expense, trauma, and risk of an irreversible procedure and then find out that it does not improve function. It is also discouraging to the physician to deal with the dissatisfied patient for whom he has recommended the procedure. Non surgical treatments includes use of a vacuum chamber to expand the penis followed by a constrive cuff at the base.

U.S. Pat. No. 4,407,275 issued Oct. 4, 1983 to Schroeder discloses a semi rigid annular ring having individual expandable chambers on the internal wall that is applied to the outside of the penis. A multiple lumen flexible conduit connected to the ring has individual connections for each chamber connecting to a pressure bulb and valve arrangement remote from the device for expanding and contracting the chambers in sequence in a wave fashion to allow only one chamber at a time to be pressurized, sending pressure down only one of the lumens at a time. This is a cumbersome, and complex apparatus which may allow blood to pass back to the heart while a chamber is being depressurized.

The Physiology of Physical Impotence

The penis shaft is made up of three cylindrical masses of erectile tissue covered by skin. The erectile tissue masses are composed of large venous sinusoids or spaces which are fed by blood from arteries and drained by veins. They contain very little blood when not aroused. When aroused, the arteries pump extra blood to the tissue and the penis enlarges. The veins draining the sinusoids are equipped with constrictor muscle to block off venous drainage during arousal. This causes the sinusoids to engorge with blood at arterial pressure. The inflated erectile tissue expands to fill the skin of the penis tightly, resulting in an enlarged and rigid organ.

In many cases of impotence, there is adequate arterial blood supply, but apparently inadequate closing off of the venous channels to inflate the sinusoids to maintain satisfactory rigidity or erection.

SUMMARY OF THE INVENTION

It is accordingly an object of the invention to provide a temporary, non-invasive, inexpensive device to overcome impotence that is completely under the control of the user. It is another object to provide such a device that will readily fit a user regardless of the size of the organ. It is yet another object that the device be safe and harmless and not disturbing to the user or his female partner.

The device of the invention comprises an inflatable cuff means which completely encircle the shaft of the penis at its proximal portion near the pubic bone. The cuff has a substantial length, extending distally toward the glans a distance preferably of thirty-three to fifty millimeters. The cuff is inflated with fluid by a squeeze bulb with either liquid or gas. The outer wall of the cuff does not stretch readily so that its diameter remains unchanged by inflation. The inner wall, adjacent the penis, expands during inflation so that its diameter decreases until it compresses the shaft of the penis, obstructing the venous drainage thereof. This causes the venous sinusoids to engorge with blood, causing an erection.

The entire inner wall does not expand uniformly during inflation. The device is so constructed that the proximal portion of the cuff, i.e. the portion closest to the body, expands first. Then, after the venous return is blocked, the inflation of the cuff and constriction of the shaft advances distally until the entire cuff is inflated and forced tightly against the shaft. This action forces the trapped blood into a smaller portion of the shaft, further expanding the sinusoids and enhancing rigidity. The penis is hard and capable of normal coitis with the device in place with normal sensations. It is not ordinarily felt by the female.

When fluid pressure is released by the user, the cuff deflates, and the penis becomes flaccid. The device is removed for later reuse. It causes no permanent changes to the penis. If it is not successful, no harm has been done. Ordinarily, the user must be sexually aroused by massage, foreplay, or by use of a vacuum chamber before inflating the cuff for successful operation. The inflatable cuff is a sequentially activated tourniquet which constricts the shaft progressively along the proximal to distal axis.

The cuff is inflated by means of a hand operated pressure bulb connected to the cuff by a single lumen tube. The sequential filling of the individual chambers, beginning at the proximal end and progressively pressurizing chambers distally is controlled by internal valves in the cuff. The bulb and single lumen tube may be detached from the cuff after all the chambers have been inflated, before intercourse for enhanced sensory experience. A check valve and quick disconnect simplify this procedure.

These and other objects, advantages and features of the invention will become more apparent when the detailed description is studied in conjunction with the drawings, in which:

BRIEF DESCRIPTION OF THE DRAWINGS

FIG. 1 is a side elevation view of a device of the invention.

FIG. 2 is a side elevation view, partially broken away, of a device of the invention.

FIG. 3A is a sectional view taken on line 99—99 of FIG. 1.

FIG. 4A is a sectional view taken on line 99—99 of FIG. 1 with another internal structure in uninflated condition.

FIG. 4B is a sectional view of the device of FIG. 4A in one-third inflated condition.

FIG. 4C is a sectional view of the device of FIG. 4A in two-thirds inflated condition.

FIG. 4D is a sectional view of the device of FIG. 4A in fully inflated condition.

FIG. 5A is a sectional view taken on line 99—99 of FIG. 1 with another internal structure.

FIG. 6 is an exploded perspective view of the device of FIG. 2.

FIG. 7 is an exploded perspective view of another embodiment of the invention.

FIG. 8A is a view as in FIG. 4A of an embodiment with a non-resilient inner surface layer.

FIG. 9 is a diagrammatic illustration of another embodiment of the invention in plan view.

FIG. 10 is a sectional view through line 10—10 of FIG. 9.

FIG. 11 is a sectional detail view of a valve of FIG. 9 in filling mode.

FIG. 12 is a sectional view as in FIG. 11 with valve in emptying mode.

FIG. 13A is a diagrammatic sectional view of another valve in closed mode.

FIG. 13B is a view as in FIG. 13A in filling mode.

FIG. 13C is a view as in FIG. 13A in emptying mode.

FIG. 14A is a diagrammatic sectional view of another valve in closed mode.

FIG. 14B is a view as in FIG. 14A in filling mode.

FIG. 14C is a view as in FIG. 14A in emptying mode.

FIG. 15A is a diagrammatic view of a valve arrangement with a middle chamber filling.

FIG. 15B is a view as in FIG. 15A with first chamber filling.

FIG. 15C is a view as in FIG. 15A with chambers emptying.

FIG. 15D is a sectional view taken through line 1 of FIG. 15A.

FIG. 16A is a diagrammatic view of a valve arrangement with middle chamber filling.

FIG. 16B is a view as in FIG. 16A with first chamber filling.

FIG. 16C is a view as in FIG. 16A during emptying.

FIG. 16D is a sectional view taken through line 2—2 of FIG. 16A.

DETAILED DESCRIPTION OF PREFERRED EMBODIMENTS

Referring now first to FIGS. 1, 2 and 4A, B, C and D, a penis 1 is shown in phantom with a shaft 2 and arrow 3 indicating the proximal to distal axis and the inflatable penile erection device 4 of the invention enclosing the shaft 2 at its base 5. The device 4 is comprised of an inner circumferential surface layer 6 of a thin, resilient, stretchy material. Surrounding the inner surface layer are a series of parallel spacer bands 7, and surrounding the spacer bands is an outer, less stretchy, circumferential surface layer 8 which together define three parallel annular expandable spaces 9, 10, 11. An inflating bulb 12 and quick disconnect check valve 13 are connected through single lumen tube 14 to the first space 9 at connection 21. Squeezing the bulb forces fluid, either liquid such as water or gas such as air, into the first space 9 under pressure causing the space to expand. The inner circumferential surface layer being thinner and more stretchable than the outer circumferential surface layer, it stretches inward, reducing the inside diameter 15 which is forced against the penile shaft at its base 5, thereby constricting the venous return from the penis and trapping blood therein as shown in FIG. 4B. A valve 16 provides a fluid communication between space 9 and space 10. After space 9 is expanded, when pressure in space 9 reaches a preset value, fluid moves through valve 16 into space 10 which expands as it fills as shown in FIG. 4C. When space 10 is filled, pressure builds up to another higher preset value, and fluid moves from space 10 through a second valve 17 into space 11 which then fills and expands as shown in FIG. 4D. As spaces 10 and 11 expand sequentially and distally in the direction of arrow 3 along the proximal to distal axis, the shaft is further compressed, causing the trapped blood to be forced distally along the shaft, increasing the turgor and rigidity of the penis. The device may be constructed from a series of endless bands cemented together.

FIG. 6 illustrates another embodiment in which three rectangular strips are joined together, a thin, resilient, stretchy, inner strip 18, a thick, non-stretchy, outer strip 19, and a spacer strip 20 sandwiched between the two which provides the partitions 7, dividing the assembly into three parallel expandable spaces 9, 10 and 11. Fastening means 22 and 23 at the opposite ends of the assembled strip provide means for joining the two ends together after the device is wrapped around the penis. This permits adjustment to organs of different diameters. The fastening means may be hook and loop fasteners, adhesives or other means well known in the art. The bulb 12 and single lumen tube 14 are connected to the first expandable space 9. Fluid connection valve 16 provides for filling of space 10 only after space 9 is pressurized. Fluid connection valve 17 provides for filling space 11 only after space 10 is pressurized.

FIG. 7 shows another embodiment of the invention in which an extruded three channel tube 24, preferably molded of a thermoplastic elastomer, is formed into a circular band 25 with connector 26 providing selective access to the three expandable channels 9, 10 and 11 via rotation of internal valve plug 27 which is provided with fluid under pressure through a pressure bulb and single lumen tube as shown above. With this system, the valve connects the pressurizing fluid first to space 9 until it is expanded. The plug 27 is then rotated until space 9 is sealed and space 10 is connected to the fluid source until it is expanded. The plug is then rotated until space 10 is also sealed and space 11 is connected. After the space 11 is expanded, the plug is again rotated to seal space 11 also, to produce effective erection of the penis. FIG. 3A shows an embodiment in which a single expandable space 28 is provided with an inner stretchable circumferential surface which is thinner and more stretchable at its proximal end 29 and becomes thicker and progressively less stretchable toward the distal end 30 thereof. As shown in phantom, the inner diameter becomes reduced progressively from proximal to distal end of the cuff as the inner surface layer stretches under the force of the inflating fluid.

Referring now to FIG. 5A, an embodiment is shown in which three expandable spaces 9, 10 and 11 are provided with increasing thickness of the resilient inner layer 31 from proximal to distal ends of the cuff. When the spaces are pressurized simultaneously, space 9 will expand first, followed by space 10 and then space 11.

The device is typically formed of a soft, resilient, stretchable elastic material having a durometer of 30 and a 2000 P.S.I. tensile strength such as natural rubber, silicone rubber, polyurethane or thermoplastic elastomer.

Referring now to FIG. 8 an embodiment is shown in which the inner layer 32 as well as well as the outer layer 33 is made of a non-stretchable material such as polyester providing a flaccid inner surface layer with enlarged spaces 9, 10, 11. When not pressurized, these spaces are readily collapsed as shown. The fluid transfer means is arranged to pressurize the three spaces sequentially, along the proximal to distal axis as shown, for example, in FIG. 7.

Referring now to FIGS. 9 and 10 a tourniquet 40 of the invention is provided with hook and loop fasteners 22, 23 to form a cuff adjustable to various diameters, with three expandable spaces 9, 10, 11 arranged to be expanded in that sequence, while space 9 is positioned most proximal. A quick connect check valve/release valve 21 connects a single lumen flexible tube 14 to a pressure generating squeeze bulb 12. Pressure flows from the bulb, through tube 14 and valve 21 into space 9. As pressure builds up, the flexible inner wall 6 inflates inward compressing the shaft until pressure is greater than venous pressure but less than arterial pressure. This simulates the physiological erection process in which the penis becomes engorged with blood as blood enters the organ but cannot leave. When pressure reaches a preset value at valve 41 it opens so that pressurizing fluid enters and inflates space 10 constricting the engorged penis distal to the constriction from space 9. This forces some of the trapped blood more distally to further enlarge and stiffen the organ.

When pressure reaches a preset value at valve 42, it opens so that pressurizing fluid may enter space 11, further constricting the penis distally and forcing more blood distally. The cuff may be made with any number of constricting bands. The valves 41 and 42 may be arranged so that valve 41 opens at a first preset pressure and valve 42 opens at a second preset pressure greater than the first. Alternatively, they may open at the same pressure, relying upon the fact that considerable pressure cannot build up at the input of a valve until the space open to it is filled. The opening pressures are preset at a value below the usual arterial pressure.

A combined preset check valve and release valve 44 is shown in the filling mode at FIG. 11 and the release mode at FIG. 12. Pressure at inlet 43 must be great enough to overcome bias spring 45 to lift ball 46 from seat 47 in order to fill a space. Input pressure keeps flap valve 48 closed. When input pressure drops below a preset value, flap valve 48 opens, to release the pressure after use.

FIGS. 13A, 13B and 13C show another valve configuration serving a similar purpose, with flap valve 49 in ball 46. Input pressure not great enough to open the valve in FIG. 13A, great enough to open the valve at FIG. 13B and the releasing mode at FIG. 13C.

FIGS. 14A, B and C show an alternative valve with a resilient body 49 providing the necessary spring bias.

The valve arrangement of FIGS. 15A-C show a valve cover flap 50 which closes off orifice 51 until the space expansion pulls the flap away from the orifice. This arrangement ensures that the valve won't open until the preceding space is inflated.

The valve arrangement of FIGS. 16A-C show a deformable slit opening 52 between spaces. As a space 53 inflates, the slit deforms enough to open a channel to the next space 54. When inlet pressure is released, the pressure slowly leaks out through the narrow slits. The user may simply open the fasteners to release the entire cuff so that slow deflation is not a problem.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A penile erection device for external application to the shaft of a penis, the device comprising:

an inflatable cuff means for completely encircling a shaft of a penis at the penile base, said cuff means, when positioned on a penile shaft, extending along a proximal to distal axis of said shaft, and having at least two volume expandable annular spaces defined by an outer circumferential surface layer and an inner circumferential surface layer;

said outer circumferential surface layer being substantially fixed and forming a substantially unchangeable outer diameter and said inner circumferential surface layer being changeable and forming an inner diameter which is varied by changing the volume of said at least two volume expandable annular spaces and construction circumferential pressure is thereby applied to said shaft as said space is expanded; and means for inflating said at least two volume expandable annular spaces in a sequential manner along said proximal to distal axis, whereby said shaft is first constricted proximally and then progressively constricted distally to thereby enhance rigidity of said shaft, said means for inflating including pressure means remote from said cuff means and a flexible conduit having a single lumen connecting said pressure means and said cuff means;

in which said cuff means includes a plurality of separate volume expandable annular spaces arranged parallel to one another along said proximal to distal axis and said means for inflating is arranged to inflate said plurality of spaces in sequence along said proximal to distal axis while maintaining pressure in spaces already inflated to thereby trap venous blood and force said trapped blood distally.

2. The device according to claim 1, further comprising valve means within said cuff means for sequentially inflating said annular spaces and maintaining said annular spaces in inflated condition.

3. The device according to claim 2 in which said valve means is arranged to delay pressurizing of a space until spaces earlier in sequence have been pressurized.

4. The device according to claim 3 in which all of said valve means are arranged to open for pressurizing at a pressure below arterial pressure to permit arterial blood to flow into the distal penis.

5. The device according to claim 4 in which said valve means are arranged to open at increasing preset pressures in a proximal to distal direction.

6. The device according to claim 4, further comprising pressure relief means arranged for deflating said spaces after use.

7. The device according to claim 5, further comprising pressure relief means arranged for deflating said spaces after use.

8. The device according to claim 1 in the form of an elongate rectangular strip having two long sides and two short sides, having fastening means connected to said short sides for fastening said two short sides together to thereby form an annular cuff of a diameter adjusted to a particular penis size.

9. The device according to claim 8 in which said fastening means includes hook and loop fasteners.

10. The device according to claim 8 in which said fastening means includes adhesive means.

11. A penile erection device for external application to the shaft of a penis, the device comprising:
- an inflatable tourniquet means for completely encircling a penile shaft at the base thereof, said tourniquet means when positioned on a penile shaft having a proximal to distal axis, extending at least about thirty-three millimeters along said proximal to distal axis and having an inner diameter adjacent said shaft;
- a plurality of expandable annular spaces within said tourniquet means, said spaces arranged parallel to one another along said axis;
- each of said spaces being provided with a resilient, stretchable inner wall defining an inner diameter of the annular space, said inner diameter being reduced when said space is pressurized by a fluid; and
- means for inflating said spaces with a pressurizing fluid in a sequential manner along said proximal to distal axis in a proximal to distal direction, whereby the inner diameter of said tourniquet means is sequentially reduced and the penile shaft is sequentially constricted along said axis until all of said spaces are inflated to thereby enhance rigidity of the penis by trapping blood and forcing it distally;
- said means for inflating including a pressure source remote from said tourniquet means and a single lumen flexible conduit means in fluid communication with said pressure source and said tourniquet means.

12. The device according to claim 11 in which said tourniquet means is constructed from an elongate rectangular strip having fastening means for forming a circular band about a penis, for adjusting to various sizes of organs.

* * * * *